(12) United States Patent
Kysilka et al.

(10) Patent No.: US 7,605,282 B2
(45) Date of Patent: Oct. 20, 2009

(54) PROCESS FOR THE PREPARATION OF AN OXALIPLATIN PREPARATION

(75) Inventors: Vladimir Kysilka, Brno (CZ); Tomas Kalisz, Praha (CZ); Petr Kacer, Phaha (CZ)

(73) Assignee: Vuab Pharma A.S. (CZ)

( * ) Notice: Subject to any disclaimer, the term of this patent is extended or adjusted under 35 U.S.C. 154(b) by 37 days.

(21) Appl. No.: 11/911,076

(22) PCT Filed: Apr. 9, 2005

(86) PCT No.: PCT/EP2005/003746

§ 371 (c)(1),
(2), (4) Date: Jan. 11, 2008

(87) PCT Pub. No.: WO2006/108428

PCT Pub. Date: Oct. 19, 2006

(65) Prior Publication Data

US 2008/0319061 A1    Dec. 25, 2008

(51) Int. Cl.
*C07F 15/00* (2006.01)
*A61K 31/28* (2006.01)

(52) U.S. Cl. .................................. 556/137; 514/492

(58) Field of Classification Search ............... 556/137; 514/492
See application file for complete search history.

(56) References Cited

U.S. PATENT DOCUMENTS 6,306,902 B1 * 10/2001 Anderson et al. ............ 514/492

FOREIGN PATENT DOCUMENTS

| EP | 0 617 043 A | 9/1994 |
|---|---|---|
| EP | 0 625 523 A | 11/1994 |
| EP | 0 801 070 A | 10/1997 |
| EP | 0 881 226 A | 12/1998 |
| WO | WO-03/004505 | 1/2003 |
| WO | WO-2005/035544 | 4/2005 |

OTHER PUBLICATIONS

Jerremalm et al., Journal of Pharmaceutical Sciences, vol. 91, No. 10, pp. 2116-2121 (2002).*
Kidani Y et al.: "Antitumor activity of 1,2-diaminocyclohexane-platinum complexes against sarcoma-180 ascites form"; Journal of Medicinal Chemistry, vol. 21, No. 12, 1978, pp. 1315-1318.

* cited by examiner

*Primary Examiner*—Porfirio Nazario Gonzalez
(74) *Attorney, Agent, or Firm*—Dickstein, Shapiro, LLP.

(57) ABSTRACT

The present invention relates to an improved process for the preparation of oxaliplatin, the obtained oxaliplatin preparation and its use in cancer therapy.

20 Claims, No Drawings

PROCESS FOR THE PREPARATION OF AN OXALIPLATIN PREPARATION

The present invention relates to a process for preparing oxaliplatin, to an oxaliplatin preparation of high purity and its use in the treatment of cancer.

Oxaliplatin, CAS Number [61825-94-3], is the generally used name for the (SP-4-2)-[(1R,2R)-1,2-cyclohexanediamine-kN,kN']-(oxalate-O,O')-platinum (II) complex of the structural formula I:

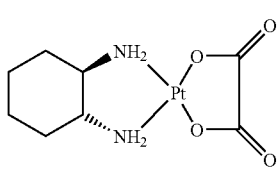

(I)

Oxaliplatin was first reported by the Nagoya City University, Japan, in Gann, 1976, 67(6), 921-2. Oxaliplatin is frequently used in cancer therapy. A general method for preparing oxaliplatin is described in U.S. Pat. No. 4,169,846. The process described is based on the reaction of a (SP-4-2)-dichloro-[(1R,2R)-1,2-cyclohexanediamine-kN,kN']platinum (II) complex (in the following abbreviated as DACHPtCl$_2$) in water with two equivalents of silver nitrate, an elimination of the obtained solid phase and a subsequent reaction of the obtained ionic platinum diaqua-complex with oxalic acid and/or its alkali metal salts. The ionic platinum (II) diaqua-complex described above can thus be considered as a key synthetic intermediate. It has the structural formula II and it is usually in the form of a dinitrate salt:

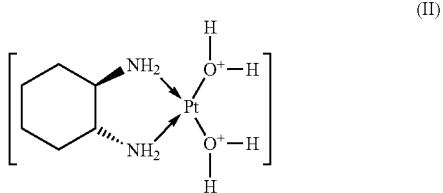

(II)

The aqueous solution containing the ionic platinum diaqua-complex II exhibits a pH of about 2 due to the acidic protons of the complex.

The yield of the finally obtained oxaliplatin is usually about 70%. Oxaliplatin prepared in such a way is, however, accompanied with various synthetic impurities, e.g. oxalic acid, DACHPtCl$_2$, Ag$^+$ ions and analogous hydroxo-bridged dimeric and trimeric platinum complexes being formed from ionic platinum (II) mono- and diaqua-complex intermediates.

The analogous impurity hydroxo-bridged dimeric platinum complex described above has the structural formula (III):

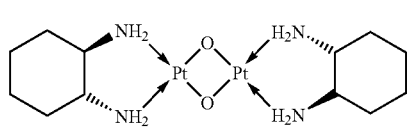

(III)

The dimeric platinum complex with the structural formula III is formed from platinum complex with the structural formula II (in the following: ionic platinum (II) diaqua complex) at a pH range of about 4 to 9 by splitting off one acidic proton from the ionic platinum (II) diaqua-complex and the subsequent condensation of such two species. The dimeric platinum complex III (in the following: dimeric platinum complex III) represents a detectable impurity in the final oxaliplatin. Any of the above-identified impurities, in particular the dimeric platinum complex III, may cause severe adverse effects in the therapeutic use of oxaliplatin. Their presence is to be avoided. Therefore, corresponding purification procedures are the subject of a great wealth of patents and patent applications. Among the most preferred purification processes are those, which use alkaline iodides for the elimination of ionic impurities from the ionic platinum (II) diaqua-complex in combination with a large amount of water for the required re-crystallization and washing of the crude product. Such a process is described for example in EP 0 617 043 B1, WO 03/004505 and EP 0 625 523 B1.

For the satisfactory elimination of the Ag$^+$ ions and other ionic impurities including an ionic platinum monoaqua-complex present in the ionic platinum (II) diaqua-complex, an about threefold excess of iodides is usually recommended. A serious drawback is, however, that iodides parallelly and predominantly react with a surplus of reactive ionic platinum (II) diaqua-complex to the corresponding platinum (II) diiodo complex. These iodo species then react with the spots of Ag$^+$ ions to form insoluble silver iodide precipitates. That is why this chemical purification method requires a considerable time, usually more than 15 hours, to reduce the content of Ag$^+$ ions below 5 p.p.m. This purification also causes a considerable loss of oxaliplatin and leads to the contamination and coloration of the product by platinum (II) mono- and diiodo complexes. Moreover, this chemical purification procedure does not eliminate analogous hydroxo-bridged dimeric platinum complex III. The crude oxaliplatin must therefore be re-crystallized from water. A further resulting serious drawback is based on the very low solubility of oxaliplatin in any solvent. A large amount of water and a temperature around the boiling point of water are necessary for the re-crystallization of the crude oxaliplatin. Finally, at the boiling point of water side products are easily formed from oxaliplatin even during the short time of the exposure, which represents another serious drawback. The yields of the re-crystallization of the product vary around 70%. If a repeated re-crystallization is necessary, a further loss of the product results.

As follows from the above mentioned prior art, there is a great demand for a process to prepare oxaliplatin in a high purity by an effective method.

The technical problem underlying the present invention is therefore to provide a process for preparing oxaliplatin, which is simple and provides oxaliplatin with a high purity and simultaneously in a high yield.

The present invention solves the above-identified technical problem by providing a process for preparing oxaliplatin of the structural formula I

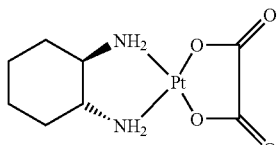

(I)

comprising the following steps:
a) Reacting a (SP-4-2)dihalogen-[(1R,2R)-1,2-cyclohexanediamine-kN,kN']platinum (II) complex with a silver salt in an aqueous medium, in particular water, to obtain an aqueous solution containing an ionic platinum (II) diaqua-complex (structural formula II) and a solid phase,
b) removing the solid phase,
c) adjusting the pH-value of the aqueous solution containing the ionic platinum (II) diaqua-complex (structural formula II) obtained in step b) to a pH-value of 9.5 to 13, to obtain an alkaline solution comprising a (SP-4-2) dihydroxo-[(1R,2R)-1,2-cyclohexanediamine-kN,kN'] platinum (II) complex (further DACHPt(OH)$_2$),
d) purifying the alkaline solution to obtain a purified alkaline solution and
e) adding oxalic acid and/or an oxalic salt to the purified alkaline solution obtained in step d) to obtain purified oxaliplatin.

The pH-adjustment of the solution containing the ionic platinum (II) diaqua-complex intermediate with the structural formula II to a pH-value of 9.5 to 13, preferably 10 to 12, leads to the formation of a stabilized analogous (SP-4-2)dihydroxo-[(1R,2R)-1,2-cyclohexanediamine-kN,kN']platinum (II) complex (DACHPt(OH)$_2$) which is relatively inert and non-ionic. DACHPt(OH)$_2$ is not stable at a pH below 9.5 due to the formation of dimeric platinum complex III. Pure DACHPt(OH)$_2$ is not also stable at a pH above 9.5 due to the formation of black precipitates but it is stabilized at this pH in the presence of anionic ligands, e.g. nitrates which are present in the ionic platinum (II) diaqua complex.

Thus, the invention provides in the process to obtain oxaliplatin a stabilized intermediate, which in turn can be subjected to various purification steps, which otherwise would not be possible, or which would cause the formation of further impurities or a loss of product. The stabilized aqueous alkaline solution of "in situ" formed DACHPt(OH)$_2$ represents a most preferred intermediate for its further purification by a chemical reaction and/or by a physical sorption before the addition of the oxalic acid and/or an oxalic salt and the formation of the final oxaliplatin. It was further found that the pH-adjustment step concurrently leads to the conversion of undesirable analogous hydroxo-bridged dimeric platinum complex III back to DACHPt(OH)$_2$. The present pH-adjustment step also leads to the precipitation of rests of solubilized or un-reacted silver salts, which can be easily removed. The pH-adjustment can be made by common and generally known procedures, e.g. by the addition of sodium hydroxide solution and/or sodium carbonate.

Thus, the present invention provides a process for preparing oxaliplatin in an improved yield and improved purity. One further preferred embodiment of the present invention solves the above-identified problem with the above-identified process, wherein such a process provides a yield of oxaliplatin, which may be comparable or even worse in comparison to the prior art methods, but wherein the purity is improved, i.e. higher than in the prior art. Compared to other prior art, the present invention solves the problem in another preferred embodiment, wherein the purity may be comparable or even worse in comparison to the prior art, but wherein the yield is improved, i.e. higher than in the prior art.

According to the present invention, the present process solves the above problem by employing a pH-value-adjustment step, according to which the pH-value of the aqueous solution comprising the ionic platinum (II) diaqua-complex obtained in steps a) and b) above is adjusted to a pH-value of 9.5 to 13, in particular to a pH-value of 10 to 12 and subsequently the obtained alkaline solution comprising the stabilized intermediate DACHPt(OH)$_2$ is purified to obtain a purified alkaline solution comprising a purified (SP4-2) dihydroxo-[(1R,2R)-1,2-cyclohexanediamine-kN,kN'] platinum (II) complex (DACHPt(OH)$_2$) and a solid phase to be removed. Using this teaching, it is possible to, in an efficient manner, obtain a high purity oxaliplatin without the need of adding iodides to the instable ionic platinum (II) diaqua-complex and, in a further embodiment of the present invention, without the need of a recrystallisation of the crude product using, for example, a large amount of boiling water.

The present invention in particular provides in a preferred embodiment the advantage that all of its process steps can be carried out using conventional water, or, in a particularly preferred embodiment, destined water as an aqueous medium in step a) above. According to the present invention, it is not necessary to use deoxygenated water in any of its process steps. The present invention therefore provides a process for preparing oxaliplatin, according to which no deoxygenated water is used. In a particularly preferred embodiment, the process of the present invention is carried out under standard environmental conditions, in particular all and each process step of the present process is carried out in an environment, which is not using specific conditions, such as: a low oxygen atmosphere, or a vacuum, or an inert gas; or a nitrogen atmosphere, or a low oxygen atmosphere. The oxidizing power of spots of free oxygen present e.g. in water is negligible with respect to nitrates and/or nitric acid being present in stoichiometric amount during the preparation of the ionic platinum (II) diaqua-complex and/or oxaliplatin.

Thus, the present invention provides in a simple manner a preparation of oxaliplatin, which is highly pure, in particular, essentially pure. In the context of the present invention, "essentially pure" means that the oxaliplatin preparation obtained has a purity of at least 97.5%, preferably at least 98%, preferably at least 98.5%, even more preferably at least 99%, most preferably at least 99.5% (percentage values given according to the present teaching are mass %, i.e. mass/mass or weight/weight, i.e. w/w percentage determined by HPLC, if not otherwise indicated), that means other compounds except for the oxaliplatin are present only in the above identified specified minor amounts. In another preferred embodiment, the degree of impurity is in overall terms most preferably at maximum 2.5%, 2.0%, or 1.5%, more preferably at maximum 1.0%, in particular 0.5%.

In particular, the present invention provides an oxaliplatin preparation according to the above-identified purity, wherein analogous hydroxyo-bridged dimeric platinum complex III is essentially missing, i.e. is present at maximum in an amount from 0.00 to 0.08%, preferably less than 0.08%, or preferably is completely missing.

In a preferred embodiment, the amount of oxalic acid (reaction component) in the oxaliplatin preparation is at maximum 0.2%, in particular at maximum 0.1%, more preferably at maximum 0.05%.

The amount of ionic platinum II diaqua-complex (synthetic intermediate) in the oxaliplatin preparation is in a preferred embodiment at maximum 0.30%.

The amount of dihydroxy platinum IV-complex (product of oxidation of oxaliplatin) in the oxaliplatin preparation is in a preferred embodiment at maximum 0.05%.

Thus, in a preferred embodiment of the present invention, the subject-matter of this invention is a simple and effective method for the preparation of oxaliplatin of the structural formula I:

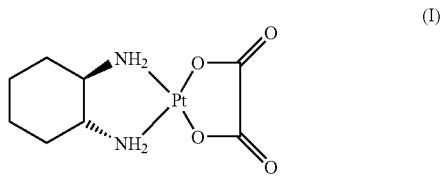

by the reaction of a (SP-4-2)dihalogen-[(1R,2R)-1,2-cyclohexanediamine-kN,kN']platinum (II)-complex with a corresponding amount of a silver salt, removal of the solid phase, i.e. in particular the precipitated silver compounds, in particular halogenid, and reaction of the corresponding ionic platinum (II) diaqua-complex (structural formula II), with oxalic acid or its salts, wherein the pH-value of the corresponding ionic platinum (II) diaqua-complex is adjusted to 9.5 to 13, the resulting solution is purified by chemical reaction and/or by physical sorption until the desired purity is reached, oxalic acid and/or oxalic salts is/are then added and the final oxaliplatin is separated in a high purity and yield. Oxaliplatin prepared according to the invention has a high purity and needs no additional re-crystallization steps from water.

In a preferred embodiment of the present invention DACHPtCl$_2$ can be used as a starting material, i.e. as (SP-4-2)dihalogen-[(1R,2R)-1,2-cyclohexanediamine-kN,kN'] platinum (II) complex.

In a further preferred embodiment of the present invention, the silver salt used in step a) is used in a stoichiometric amount in relation to the starting platinum (II) complex, e.g. per molar equivalent of the starting platinum (II) complex two molar equivalents of the silver nitrate or one molar equivalent of silver sulphate are used.

In a further preferred embodiment of the present invention the silver salt used in step a) is silver nitrate (AgNO$_3$) or silver sulphate (Ag$_2$SO$_4$).

In a preferred embodiment of the present invention, the content of Ag$^+$ in the alkaline solution purified in step d) is less than 0.1 ppm before adding oxalic acid and/or an oxalic salt in step e).

In a particularly preferred embodiment of the present invention, in step d), that means for the purification of the alkaline solution to obtain a purified alkaline solution 1, 2, 3 or more different or identical purification steps are conducted. According to the present invention it is possible to use physical and/or chemical means, for instance adsorptive and/or absorptive materials and/or chosen anionic ligands to purify the alkaline solution comprising the stabilized DACHPt (OH)$_2$ intermediate in order to remove impurities.

In one preferred embodiment of the present invention, it is for instance possible to use active carbon, in particular to improve the filtration of silver precipitates and to remove non-polar impurities. In addition or instead of using the active carbon, silica gel and/or aluminium oxide and/or aluminium silicate and/or chemical means, e.g. oxalate anions or carbonate anions or phosphate anions can be used separately or together in combination. In a particularly preferred embodiment of the present invention the purification in step d) is conducted by using a mixture of active carbon and silica gel. Such a combination considerably decreases the content of Ag.sup.+ in the alkaline solution of DACHPt(OH)$_2$ as well as the content of related impurities. Furthermore, the solution is decolourised.

In a particularly preferred embodiment of the present invention three cycles of purification are conducted using mixtures of active carbon and silica gel which leads to a pure and colourless alkaline solution of DACHPt(OH)$_2$.

In a furthermore preferred embodiment of the present invention, the purification in step d) is conducted using a mixture of active carbon, silica gel and oxalate or carbonate anions, in particular sodium oxalate or sodium carbonate. In a preferred embodiment of the present invention two purification cycles are conducted using mixtures of active carbon and silica gel together with oxalate anions, in particular sodium oxalate, which leads to a pure and colourless alkaline solution of DACHPt(OH)$_2$.

In a preferred embodiment of the present invention, the above-identified purification steps are each followed by a process step to remove the solid phase, for instance by filtration or centrifugation. It is also possible to carry out the purification procedure on column with said sorbents.

A purification of the obtained alkaline solution from impurities, including spots of Ag$^+$ ions, can further be performed in a preferred embodiment by the use of for example a cationic exchange resin, preferably in Na$^+$ cycle, with a subsequent removal of the solid phase. In a further preferred embodiment of the present invention the active carbon and/or silica gel and/or aluminium oxide and/or aluminium silicate and/or chemical means, e.g. oxalate anions or carbonate anions or phosphate anions can be used instead of or in addition to the cationic exchange resin. L-cystein and/or iodides can be used instead of e.g. oxalate anions, but their rest must be removed before addition of oxalic acid, for example by an anion exchange resin in OH$^-$ cycle. These chemical purification procedures have a negligible effect on the relatively inert and non-ionic DACHPt(OH)$_2$ and so, there is negligible loss of the final oxaliplatin, too. The alkaline solution of the non-ionic DACHPt(OH)$_2$ can in a further preferred embodiment of the present invention be purified by physical sorption by means of non-polar and/or polar sorbent. In a further preferred embodiment of the present invention active carbon can be used as a non-polar sorbent for the elimination of non-polar impurities from this intermediate. In a further preferred embodiment of the present invention silica gel and/or aluminosilicate and/or aluminium oxide can be used as a polar sorbent for the elimination of polar and other impurities from this intermediate.

In a preferred embodiment of the present invention, the above-described purification procedures can be repeated once or more times before addition of the oxalic acid and/or the oxalic salt until the desired purity is reached without substantial loss of the product.

In a further preferred embodiment of the present invention, oxalic acid in an amount of 1.0 to 3.0 equivalents with respect to starting DACHPtCl$_2$ is preferred for the conversion to oxaliplatin in a high purity and yields. The conversion takes place in a preferred embodiment of the invention for 2 to 6 hours, preferably at room temperature.

It is advantageous in a further preferred embodiment of the present invention to wash the final oxaliplatin, for example by repeatedly using small amounts of water to remove inorganic salts and, in a further embodiment, then repeatedly by bigger amounts of for example an aliphatic alcohol, e.g. ethanol. Oxalic acid is soluble in ethanol and its excess can be effectively removed by such a procedure. Oxaliplatin is practically insoluble in ethanol and so, there is also a negligible loss of the desired product.

It is advantageous in a further preferred embodiment to add hydrochloric acid to the waste water from oxaliplatin filtration and washing to recover the preferred starting material $DACHPtCl_2$ in a high purity and moderate amount. It improves efficacy of the process according to invention, too.

The process of the present invention can, in a preferred embodiment of the present invention, be conducted in water, preferably at room temperature. In a preferred embodiment of the present invention, the process is carried out in the absence of light, in particular visible light.

The present invention also provides an oxaliplatin preparation exhibiting a specific impurity profile, according to which it contains the analogous hydroxo-bridged dimeric platinum complex with the structural formula III in an amount of less than 0.08% w/w, which is obtainable according to the present invention.

The present invention also foresees a process for preparing such an intermediate comprising the above-identified steps
  a) reacting a (SP-4-2)dihalogen-[(1R,2R)-1,2-cyclohexanediamine-kN,kN'] platinum (II) complex with a silver salt in an aqueous medium, preferably water, to obtain an aqueous solution containing an ionic platinum (II) diaqua-complex and a solid phase,
  b) removing the solid phase,
  c) adjusting the pH-value of the aqueous solution containing the ionic platinum (II) diaqua-complex obtained in step b) to a pH-value of 9.5 to 13, to obtain an alkaline solution comprising (SP-4-2)dihydroxo-[(1R,2R)-1,2-cyclohexanediamine-kN,kN']platinum (II) complex $(DACHPt(OH)_2)$, and optionally d), purifying the alkaline solution to obtain a purified alkaline solution and isolating the stabilized intermediate $DACHPt(OH)_2$ therefrom, wherein a purified $DACHPt(OH)_2$ is obtained.

The present invention also foresees a pharmaceutical composition comprising an oxaliplatin preparation of the present invention together with at least one pharmaceutically acceptable carrier and optionally further additives.

Furthermore, the present invention provides the use of an oxaliplatin preparation according to the present invention for the preparation of a pharmaceutical composition for the treatment of cancer.

The invention will be further explained in more detail by way of examples. These examples are illustrative only and do in no way limit the scope of the invention defined in the claims and the contents of the present description.

EXAMPLES

Example 1

All procedures were carried out at room temperature in the absence of light.

A mixture of 3.80 g of fine powdered 97% $DACHPtCl_2$ (9.7 mmol), 3.33 g 99% $AgNO_3$ (19.4 mmol) and 38 ml water was intensively agitated for 48 hours. The solid fraction was then removed and a cake was properly sucked. 0.1N solution of NaOH was added to the filtrate to adjust the pH to 12. Active carbon in an amount 0.3 g was added to the mixture and stirred for 1 hour. The solid fraction was removed by filtration and a cake was properly sucked. The yellow crude alkaline filtrate has the content of Ag+ 0.00252 mass. %, i.e. 22 ppm. 0.08 g of sodium oxalate (0.6 mmol), 0.3 g of active carbon and 0.3 g of silica gel were then added to this filtrate, pH was adjusted to 12 again and mixture was stirred 4 hours. The solid fraction was removed by filtration and a cake was properly sucked. The near colorless filtrate has the content of Ag+ 0.2 ppm. The purification process with sodium oxalate, active carbon and silica gel was repeated one times. The clear colorless filtrate has the content of Ag+ under a detection limit. 1.1 g oxalic acid dihydrate p.a. (8.7 mmol) was added to the filtrate and the mixture was stirred for 4 hours. The final solid oxaliplatin was filtered, washed four times with 2 ml iced water and six times with 5 ml ethanol. Waste water was collected. Oxaliplatin was dried under nitrogen flow at 40° C. to the constant weight.

The yield of oxaliplatin was 2.80 g (72.7% based on starting $DACHPtCl_2$). The appearance of the product was white. The content of silver was less than 0.0001 mass %, the content of analogous hydroxo-bridged dimeric platinum complex III was 0.06%, the content of oxalic acid was 0.08% and the total content of related impurities was 0.22% (by HPLC method).

3 ml of concentrated hydrochloric acid was added to the waste water from oxaliplatin filtration and washing. 0.4 g of starting $DACHPtCl_2$ with the purity greater than 98% was recovered.

Example 2

All procedures were carried out at room temperature in the absence of light.

A mixture of 3.80 g of fine powdered 97% $DACHPtCl_2$ (7.7 mmol), 3.33 g 99% $AgNO_3$ (19.4 mmol) and 38 ml water was intensively agitated for 48 hours. The solid fraction was then removed and a cake was properly sucked. 0.1N solution of NaOH was added to the filtrate to adjust the pH to 12. Active carbon in an amount 0.3 g was added to the mixture and stirred for 1 hour. The solid fraction was removed by filtration and a cake was properly sucked. The yellow crude alkaline filtrate has the content of Ag+ 0.0025 mass. %, i.e. 25 ppm. 0.3 g of active carbon and 0.3 g of silica gel were then added to this filtrate, the pH was adjusted to 12 again and the mixture was stirred 2 hours. The solid fraction was removed by filtration and a cake was properly sucked. The near colorless filtrate has the content of Ag+ 2 ppm. The purification process with active carbon and silica gel was repeated one times. The clear colorless filtrate has the content of Ag+ 0.3 ppm. The purification process with active carbon and silica gel was repeated one times. The clear colorless filtrate has the content of Ag+ under a detection limit. 1.23 g oxalic acid dihydrate p.a. (9.76 mmol) was added to the filtrate and the mixture was stirred for 4 hours. The final solid oxaliplatin was filtered, washed four times with 2 ml iced water and six times with 5 ml ethanol. Oxaliplatin was dried under nitrogen flow at 40° C. to the constant weight.

The yield of oxaliplatin was 2.68 g (69.5% based on starting $DACHPtCl_2$). The appearance of the product was white. The content of silver was less than 0.0003 mass %, the content of analogous hydroxo-bridged dimeric platinum complex III was 0.03%, the content of oxalic acid was 0.06% and the total content of related impurities was 0.18% (by HPLC method).

Example 3

All procedures were carried out at room temperature in the absence of light.

A mixture of 3.80 g of fine powdered 97% $DACHPtCl_2$ (9.7 mmol), 3.33 g 99% $AgNO_3$ (19.4 mmol) and 38 ml water was intensively agitated for 48 hours. The solid fraction was then removed and a cake was properly sucked. 0.1N solution of NaOH was added to the filtrate to adjust the pH to 12. Active carbon in an amount 0.3 g was added to the mixture and stirred for 1 hour. The solid fraction was removed by filtration and a cake was properly sucked. The yellow crude alkaline filtrate has the content of Ag+ 25 ppm. The filtrate was poured on a column with 30 ml of wet DOWEX 50W-X8 ($Na^+$ cycle) (54 meqv.) and the eluent including necessary amount of washing water was carefully collected and partially concentrated. 0.3 g of active carbon and 0.3 g of silica gel were then added to the concentrated eluent, the pH was adjusted to 12 again and the mixture was stirred for 2 hours. The solid fraction was removed by filtration and a cake was properly sucked. The resulting filtrate was colorless and it has the content of Ag+ 0.03 ppm. 1.23 g oxalic acid dihydrate p.a. (9.76 mmol) was added to the filtrate and the mixture was stirred for 4 hours. The final solid oxaliplatin was filtered, washed four times with 2 ml iced water and six times with 5 ml ethanol. Oxaliplatin was dried under nitrogen flow at 40° C. to the constant weight. The yield was 2.50 g (164.9% based on starting $DACHPtCl_2$). The appearance of the product was white. The content of silver was less than 0.0003 mass %, the content of hydroxo-bridged dimeric platinum complex III was 0.04%, the content of oxalic acid was 0.05% and the total content of related impurities was 0.24% (by HPLC method).

Example 4

Comparative

All procedures were made at room temperature in the absence of light.

A mixture 3.80 g of fine powdered 97% $DACHPtCl_2$ (9.7 mmol), 3.33 g 99% $AgNO_3$ (19.4 mmol) and 38 ml water was intensively agitated for 48 hours. The solid fraction was then removed and the cake was properly sucked. 0.17 g potassium iodide (1 mmol) was added to the filtrate and stirred for 15 hours. Active carbon in an amount of 0.3 g was then added and the suspension was stirred for another 1 hour. The solid fraction was removed by filtration and the cake was properly sucked. 1.23 g oxalic acid dihydrate p.a. (39.76 mmol) was added to the filtrate and the mixture was stirred for 4 hours. The solid oxaliplatin was filtered, washed four times with 2 ml iced water and six times with 5 ml of ethanol. Oxaliplatin was dried under nitrogen flow at 40° C. to the constant weight. The yield was 2.40 g (62.3% based on starting $DACHPtCl_2$). The appearance of the product was light yellow. The content of silver was less than 0.0003 mass %, the content of analogous hydroxo-bridged dimeric platinum complex was 0.25%, the content of oxalic acid was 0.03% and the total content of related impurities was 0.45% (by HPLC method).

The crude product was dissolved in 105 ml water at 95-97° C. The hot solution was filtered without delay, the filtrate was cooled to 5° C. and stirred for an additional 2 hours. The final solid oxaliplatin was filtered, washed twice with 2 ml iced water and six times with 5 ml of ethanol. The oxaliplatin was dried under nitrogen flow at 40° C. to the constant weight. The yield was 1.70 g (44.1% based on the starting $DACHPtCl_2$). The appearance of the product was white. The content of silver was less than 0.0002 mass %, the content of analogous hydroxo-bridged dimeric Pt-complex was 0.12%, the content of oxalic acid was 0.02% and the total content of related impurities was 0.21% (by HPLC method).

In a preferred embodiment of the present invention, the total amount of the above-identified mentioned three impurities, oxalic acid, ionic platinum (II) diaqua complex and the dihydroxy platinum (IV) complex in the oxaliplatin preparation, is at maximum 0.30%.

Furthermore, the amount of the reverse S,S-enantiomer of oxaliplatin is in a preferred embodiment at maximum 0.2%.

The amount of hydroxo-bridge platinum-complex dimer and other detectable impurities in the oxaliplatin preparation is in a preferred embodiment at maximum 0.1%.

The amount of silver in the oxaliplatin preparation is in a preferred embodiment at maximum 5 ppm.

The very low content of analogous hydroxo-bridged dimeric platinum complex III and oxalic acid obtained according to the present invention is advantageous because these substances can cause serious side effects in the final pharmaceutical composition.

In a preferred embodiment, the total content of oxaliplatin-related impurities in the product according to the invention is less than 0.30%.

In a further preferred embodiment the total yield of the final product is at least 60%, at least 65%, at least 70%, preferably at least 72%, and most preferred at least 80% (w/w), based on the starting $DACHPtCl_2$.

The invention claimed is:

1. A process for preparing oxaliplatin of the structural formula I:

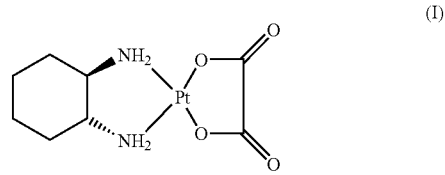

comprising the following steps:
  a) reacting a (SP-4-2)dihalogen-[(1R,2R)-1,2-cyclohexanediamine-kN,kN']platinum(II) complex with a silver salt in an aqueous medium to obtain an aqueous medium to obtain an aqueous solution containing ionic platinum (II)diaqua-complex and a solid phase,
  b) removing the solid phase,
  c) adjusting the pH-value of the aqueous solution containing the ionic platinum(II)diaqua-complex obtained in step b) to a pH-value of 9.5, to obtain an alkaline solution comprising a (SP-4-2)dihydroxo-[(1R,2R)-1,2-cyclohexanediamine-kN,kN']platinum(II) complex (DACHPt(OH)$_2$),
  d) purifying the alkaline solution to obtain a purified alkaline solution and
  e) adding oxalic acid and/or an oxalic salt to the purified alkaline solution obtained in step d) to obtain purified oxaliplatin.

2. The process according to claim 1, wherein the pH-value of the aqueous solution containing the ionic platinum(II) diaqua-complex in step c) is adjusted to 10-12.

3. The method according to claim 1, wherein the pH-value in step c) is adjusted by the addition of sodium hydroxide solution and/or sodium carbonate.

4. The method according to claim 1, wherein the alkaline solution is purified in step d) by a chemical reaction or a physical sorption or both.

5. The method according to claim 1, wherein subsequent to the purification step d) a solid phase is removed from the purified alkaline solution.

6. The process according to claim 1, wherein the alkaline solution is purified in step d) by the addition of active carbon, optionally together with a polar sorbent, and the solid phase obtained is then removed.

7. The process according to claim 1, wherein the alkaline solution is purified in step d) by the addition of oxalate anions, carbonate anions, phosphate anions or a mixture thereof and the solid phase is then removed.

8. The process according to claim 1, wherein the alkaline solution is purified in step d) by the addition of a cationic exchange resin, and the solid phase is then removed.

9. The process according to claim 1, wherein the alkaline solution is purified in step d) by the addition of oxalate anions together with at least one non-polar or polar sorbent or both and the solid phase is then removed.

10. The process according to claim 6, wherein silica gel and/or aluminium silicate and/or aluminium oxide is used as polar sorbent is at least one selected from the group consisting of silica gel, aluminium silicate and aluminium oxide.

11. The process according to claim 1, wherein the purification step d), in particular the addition and removal of oxalate anions together with any non-polar and/or polar sorbent, is repeated at least once.

12. The process according to claim 1, wherein in step e) 1.0 to 3.0 equivalents oxalic acid or oxalic salt are used with respect to starting $DACHPtCl_2$.

13. The process according to claim 1, wherein step e) is carried out for 2 to 6 hours at room temperature.

14. The process according to claim 1, wherein the purified oxaliplatin in step e) is isolated from the purified alkaline solution.

15. The process of claim 1, wherein the oxaliplatin obtained in step e) is subsequently washed at least once.

16. The process according to claim 1, wherein the oxaliplatin obtained in step e) is washed at least once and subsequently with an aliphatic alcohol.

17. The process according to claim 15, wherein hydrochloric acid is added to the waste water and the starting (SP-4-2)dichloro-[(1R,2R)-1,2-cyclohexanediamine-kN,kN']platinum(II) complex is recovered.

18. The process according to claim 1, wherein in step a) a (SP-4-2)dichloro-[(1R,2R)-1,2-cyclohexanediamine-kN,kN']platinum(II) complex is used as the starting (SP-4-2)dihalogen-[(1R,2R)-1,2-cyclohexanediamine-kN,kN']platinum (II) complex.

19. The process according to claim 1, wherein a stoichiometric amount of the silver salt in respect to the amount of the starting (SP-4-2)dihalogen-[(1R,2R)-1,2-cyclohexanediamine-kN,kN']platinum(II) complex ($DACHPtCl_2$) is used.

20. A process for preparing a stabilized non-ionic compound (SP-4-2)dihydroxo-[(1R,2R)-1,2-cyclohexanediamine-kN,kN']platinum(II) complex ($DACHPt(OH)_2$), comprising the steps a) reacting a (SP-4-2)dihalogen-[(1R,2R)-1,2-cyclohexanediamine-kN,kN']platinum(II) complex with a silver salt in an aqueous medium to obtain an aqueous solution containing an ionic platinum(II)diaqua-complex and a solid phase, b) removing the solid phase, c) adjusting the pH-value of the aqueous solution containing the ionic platinum(II)diaqua-complex obtained in step b) to a pH-value of 9.5 to 13, to obtain an alkaline solution comprising (SP-4-2)dihydroxo-[(1R,2R)-1,2-cyclohexanediamine-kN,kN']platinum(II) complex ($DACHPt(OH)_2$), and optionally d) purifying the alkaline solution to obtain a purified alkaline solution comprising the purified $DACHPt(OH)_2$ and isolating them therefrom.

* * * * *